(12) United States Patent
Lin et al.

(10) Patent No.: US 10,653,735 B2
(45) Date of Patent: May 19, 2020

(54) **USES OF *MESEMBRYANTHEMUM CRYSTALLINUM* L. CALLUS EXTRACT IN DELAYING SKIN CELL AGING, NURSING SKIN, TREATING AND PREVENTING SKIN CANCER**

(71) Applicant: TCI CO., LTD., Taipei (TW)

(72) Inventors: Yung-Hsiang Lin, Taipei (TW); Wei-Wen Kuo, Taipei (TW); I-Hui Chen, Taipei (TW); Yi-Chun Chen, Taipei (TW); Hui-Hsin Shih, Taipei (TW); Yun-Ching Tsai, Taipei (TW)

(73) Assignee: TCI CO., LTD., Taipei (TW)

( * ) Notice: Subject to any disclaimer, the term of this patent is extended or adjusted under 35 U.S.C. 154(b) by 397 days.

(21) Appl. No.: 15/462,462

(22) Filed: Mar. 17, 2017

(65) Prior Publication Data

US 2017/0274029 A1    Sep. 28, 2017

Related U.S. Application Data

(60) Provisional application No. 62/310,412, filed on Mar. 18, 2016.

(51) Int. Cl.

| | |
|---|---|
| *A61K 36/185* | (2006.01) |
| *A61Q 19/08* | (2006.01) |
| *A61K 8/9789* | (2017.01) |
| *A61K 8/97* | (2017.01) |
| *A61K 9/00* | (2006.01) |

(52) U.S. Cl.
CPC .............. *A61K 36/185* (2013.01); *A61K 8/97* (2013.01); *A61K 8/9789* (2017.08); *A61K 9/0053* (2013.01); *A61K 9/0095* (2013.01); *A61Q 19/08* (2013.01)

(58) Field of Classification Search
CPC .................................................. A61K 36/185
See application file for complete search history.

(56) References Cited

U.S. PATENT DOCUMENTS 5,595,756 A * 1/1997 Bally .................. A61K 9/1272
                                                     264/4.1
6,271,001 B1 * 8/2001 Clarke .................... A61K 8/73
                                                     435/41

OTHER PUBLICATIONS

Sporn et al. "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
Jain RK (Scientific American, Jul. 1994,58-65) (Year: 1994).*
(U1) Introduction to cancer from Merck manual, p. 1, Accessed Mar. 5, 2008. (Year: 2008).*
(V1) Clinical Aspects of Cancer from Merck manual, pp. 1-4. Accesssed Mar. 5, 2008. (Year: 2008).*
(W1) Melanoma from Merck manual, pp. 1-4. Accessed Jan. 12, 2011. (Year: 2011).*
(X1) Cancer Drug Design and Discovery Neidle, Stephen, ed. (Elsevier/Academic Press, 2008) p. 431 (Year: 2008).*

* cited by examiner

*Primary Examiner* — Amy L Clark
(74) *Attorney, Agent, or Firm* — Christensen, Fonder, Dardi & Herbert PLLC

(57) ABSTRACT

Use of *Mesembryanthemum crystallinum* L. callus extract in the manufacture of a medicament or a skin care product, wherein the medicament or skin care product is for at least one of delaying skin cell aging, nursing skin, repairing skin, treating skin cancer, and preventing skin cancer.

8 Claims, 6 Drawing Sheets
(6 of 6 Drawing Sheet(s) Filed in Color)

USES OF *MESEMBRYANTHEMUM CRYSTALLINUM* L. CALLUS EXTRACT IN DELAYING SKIN CELL AGING, NURSING SKIN, TREATING AND PREVENTING SKIN CANCER

FIELD OF THE INVENTION

The present invention relates to the *Mesembryanthemum crystallinum* L. callus extract and the uses thereof. The invention especially relates to the uses of the *Mesembryanthemum crystallinum* L. callus extract in delaying skin cell aging, nursing skin, treating and preventing skin cancer.

BACKGROUND OF THE INVENTION

Ultraviolet (UV) rays is one of the primary factors that cause aging and pathological changes to skin. Depending on the wavelength, UV can be classified as UVA, UVB, and UVC. It has been known that over 90% of UV in sunlight is UVA, which has very strong penetration and can penetrate the dermis of skin and cause damage to the skin. Frequent exposure to UVA radiation will cause skin photoaging, reactive oxygen species (ROS) production, DNA damage, collagen wasting, skin flaccidity, etc., and even skin cancer.

Photoaging refers to thickening of skin keratin, desiccation and desquamation of skin, generation of fine lines and dark spots, and skin flaccidity, and the likes due to the acceleration of skin cell aging caused by long term exposure of UV radiation. ROS production will increase oxidation stress in cells, accelerate cell aging and even cause an overactivation of matrix-degrading enzymes, and thus, lead to collagen wasting and skin flaccidity. In addition, UVA may also destroy DNA of cells and cause DNA damage. Accumulation of excessive damaged DNA may not only cause cell aging but also lead to cancerous cells, and thus, results in skin cancer.

Among the skin cancers, melanocytoma is the most lethal. Currently, surgery is the primary method for treating melanocytoma in clinic. For those who are unable to undergo surgery, there is still a need for an effective method for treating or preventing melanocytoma.

In view of the above issues, an effective method for delaying skin cell aging, nursing skin, repairing skin, treating and/or preventing skin cancer is highly desirable in the art. Inventors of the present invention found that *Mesembryanthemum crystallinum* L. callus extract is effective in reducing the cell damage caused by UV, reducing skin texture and pores, reducing transepidermal water loss, and inducing apoptosis of melanoma cells, and thus, can be used for delaying skin cell aging, nursing skin, repairing skin, treating and/or preventing skin cancer.

SUMMARY OF THE INVENTION

An objective of the present invention is to provide a use of *Mesembryanthemum crystallinum* L. callus extract in the manufacture of a skin care product, wherein the product is for at least one of delaying skin cell aging, nursing skin, and repairing skin. Preferably, the skin care product is for at least one of anti-photoaging, anti-oxidation, and repairing DNA, or for at least one of alleviating collagen degradation, alleviating collagen wasting, and reducing skin texture.

Another objective of the present invention is to provide a use of *Mesembryanthemum crystallinum* L. callus extract in the manufacture of a medicament, wherein the medicament is for at least one of treating skin cancer, preventing skin cancer. And, the skin cancer includes such as melanocytoma.

Still another objective of the present invention is to provide a method for at least one of delaying skin cell aging, nursing skin, repairing skin, treating skin cancer, and preventing skin cancer, comprising administering to a subject in need an effective amount of a *Mesembryanthemum crystallinum* L. callus extract.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
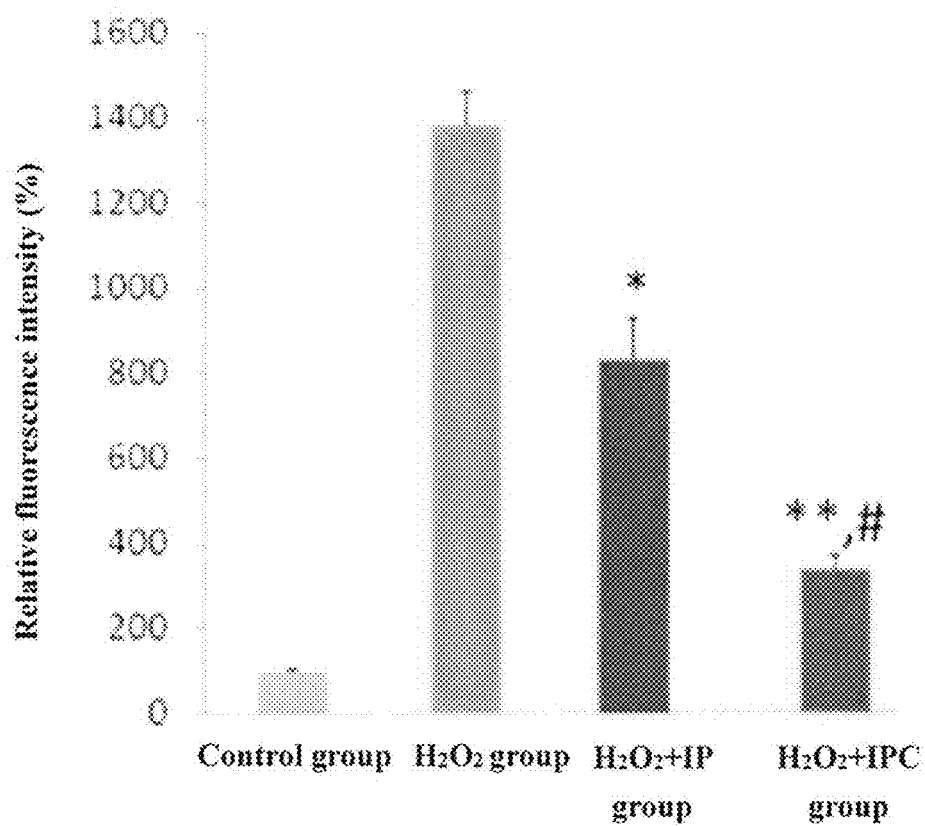
FIG. 1 shows the results of using DCF-DA dye to determine the ROS content in human skin fibroblasts.

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms.

*Mesembryanthemum crystallinum* L. is a dicotyledonous annual plant and belongs to the family of Aizoaceae and the genus of *Lampranthus*. Inventors of the present invention found that the characteristics of the calluses of *Mesembryanthemum crystallinum* L. plant generated by injury are similar to those of the pluripotent stem cells of mammals, and that the callus extract is effective in anti-photoaging, anti-oxidation, repairing DNA, alleviating collagen degradation, alleviating collagen wasting, and reducing skin texture.

Therefore, the present invention provides uses of *Mesembryanthemum crystallinum* L. callus extract in delaying skin cell aging, nursing skin, repairing skin, treating skin cancer and/or preventing skin cancer, including a use of *Mesembryanthemum crystallinum* L. callus extract in the manufacture of a skin care product for delaying skin cell aging, nursing skin and/or repairing skin, a use of *Mesembryanthemum crystallinum* L. callus extract in the manufacture of a medicament for treating skin cancer and/or preventing skin cancer, and a method for at least one of delaying skin cell aging, nursing skin, repairing skin, treating skin cancer and preventing skin cancer comprising administering *Mesembryanthemum crystallinum* L. callus extract to a subject in need.

The *Mesembryanthemum crystallinum* L. callus extract adopted by the present invention can be provided by extracting *Mesembryanthemum crystallinum* L. callus with a solvent. The solvent can be a polar solvent such as an alcohol, water, or a combination thereof. Preferably, the polar solvent is selected from C1-C4 alcohols, water, and combinations thereof. For example, the extraction could be carried out with the use of ethanol as the polar solvent. Optionally, the extraction could be carried out along with an ultrasonic operation to increase the extraction efficiency. Preferably, a drying operation could be conducted prior to the extraction.

In some embodiments of the present invention, *Mesembryanthemum crystallinum* L. callus was freeze-dried before being extracted. For example, freeze-dried *Mesembryanthemum crystallinum* L. callus could be mixed with water at a weight ratio of 100:1 (water:freeze-dried *Mesembryanthemum crystallinum* L. callus) to provide a mixture, and the mixture was subject to an ultrasonic agitation at 70° C. for 45 minutes to accomplish the extraction. Alternatively, the freeze-dried *Mesembryanthemum crystallinum* L. callus could be mixed with 70% ethanol solution at a weight ratio of 10:1 (70% ethanol solution:freeze-dried *Mesembryanthemum crystallinum* L. callus) to provide a mixture, and the mixture was subject to an ultrasonic agitation at 70° C. for 30 minutes to accomplish the extraction.

The *Mesembryanthemum crystallinum* L. callus can be provided by the following steps:
I. Washing *Mesembryanthemum crystallinum* L. plants with 6% sodium hypochlorite solution and then with sterile water, optionally, the aforementioned washing steps could be repeated;
II. Cutting the washed *Mesembryanthemum crystallinum* L. plants to create wounds on their surfaces to induce the callus generation (for 1 to 3 months); and
III. Cultivating the callus(es) obtained from step II in a MS medium (Murashige and Skoog Basal Medium, purchased from Sigma company, product number: M5519) at 25° C. and 50~60% of humidity (for 1 to 1.5 months).

According to the present invention, the *Mesembryanthemum crystallinum* L. callus extract could be an original form of the liquid extract directly obtained from extraction, or a product obtained from carrying out on the liquid extract one or more optional steps such as filtration, sterilization, concentration, dilution, etc. so as to increase the ease of use of the liquid extract. For example, a powder product being convenient for carry or storage could be provided by rendering the liquid extract to the operations such as concentrating-drying, spray-drying, or freeze-drying, etc.

Depending on the desired administration manner, the skin care product according to the present invention could be provided in any suitable form without specific limitations. For example, the skin care product could be provided in a form of an emulsion, a cream, a gel (such as a hydrogel), a paste (such as a dispersing paste, an ointment), a spray, or a solution (such as a lotion, a suspension) for external use, but is not limited thereby. Alternatively, the skin care product of the present invention could be provided in a form of a food for swallowing or drinking, such as a health food, a beauty beverage etc. In addition, the skin care product of the present invention could be also provided in a form of injection for subcutaneous administration.

Similarly, depending on the desired administration manner, the medicament according to the present invention could be provided in any suitable form without specific limitations. For example, the medicament can be administered to a subject in need by an oral or parenteral (such as transdermal, subcutaneous, intravenous, muscular, peritoneal, or nasal) route, but administration is not limited thereby. Depending on the form and purpose, suitable carriers can be chosen and used to provide the medicament, wherein the carriers include excipients, diluents, auxiliaries, stabilizers, absorbent retarders, disintegrating agent, hydrotropic agents, emulsifiers, antioxidants, adhesives, binders, tackifiers, dispersants, suspending agents, lubricants, hygroscopic agents, etc.

As a dosage form for oral administration, the medicament could comprise any pharmaceutically acceptable carriers that will not adversely affect the desired effects of the *Mesembryanthemum crystallinum* L. callus extract and/or its active components. For example, the pharmaceutically acceptable carriers can be water, saline, dextrose, glycerol, ethanol or its analogs, cellulose, starch, sugar bentonite, and combinations thereof. The medicament can be provided in any suitable form for oral administration, such as in the form of a tablet (e.g., dragee), a pill, a capsule, granules, a pulvis, a fluidextract, a solution, syrup, a suspension, a tincture etc.

As for the form of injections or drips suitable for subcutaneous, muscular, or peritoneal administration, the medicament could comprises one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the medicament as an intravenous infusion, an emulsified intravenous infusion, a powder for injection, a suspension for injection, or a powder suspension for injection, etc. Alternatively, the medicament could be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the skin care product or medicament provided according to the present invention could further comprise a suitable amount of additives, such as a flavoring agent, a toner, or a coloring agent for enhancing the palatability and the visual perception of the skin care product or medicament, and/or a buffer, a conservative, a preservative, an antibacterial agent, or an antifungal agent for improving the stability and storability of the skin care product or medicament. In addition, the skin care product or medicament could optionally further comprise one or more other active ingredient(s) (such as hyaluronic acid, mandelic acid, arbutin, collagen, elastin, etc.), or be used in combination with a skin care product or a medicament comprising one or more other active ingredients, to further enhance the effects of the skin care product or medicament, or to increase the application flexibility and adaptability of the preparation thus provided, as long as the other active ingredients or additives do not adversely affect the desired effect of the skin care product or medicament of the present invention.

Depending on the need, age, body weight, and health conditions of the subject, the skin care product or medicament provided by the present invention could be dosed at various administration frequencies, such as once a day, multiple times a day, or once every few days, etc.

When the skin care product provided in accordance with the present invention is administered to the skin surface for delaying skin cell aging, nursing skin and/or repairing skin, depending on the type of the product, the concentration of the *Mesembryanthemum crystallinum* L. callus extract comprised in the product could be varied. For example, in the case that the product is provided as an essence, the concentration of *Mesembryanthemum crystallinum* L. callus extract in the essence could range from such as 0.01 to 10 wt % (e.g. 1 wt %). On the other hand, in the case that the product is provided as a beauty beverage, and the concentration of *Mesembryanthemum crystallinum* L. callus extract in the beauty beverage could range from such as 1 to 1000 ppm (e.g. 100 ppm).

The present invention further provides a method for at least one of delaying skin cell aging, nursing skin, repairing skin, treating skin cancer, and preventing skin cancer, comprising administering to a subject in need an effective amount of a *Mesembryanthemum crystallinum* L. callus extract. In the method, according to the present invention, the applied route, applied form, suitable dosage and use of *Mesembryanthemum crystallinum* L. callus extract in related treatment or prevention are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Example 1: Preparation of Extracts

The *Mesembryanthemum crystallinum* L. seeds (purchased from Taiwan Vegetable House—Horticultural Supplies, product number. 00K20) are cultivated into *Mesembryanthemum crystallinum* L. plants. Thereafter, the plants were divided into two batches of A and B. Wherein, the *Mesembryanthemum crystallinum* L. plants of batch A was subject to the following operations to provide *Mesembryanthemum crystallinum* L. callus:
I. Washing *Mesembryanthemum crystallinum* L. plants with 6% sodium hypochlorite solution and then washing with sterile water, optionally, the aforementioned washing steps could be repeated;
II. Cutting the washed *Mesembryanthemum crystallinum* L. plants to create wounds on their surfaces to induce the callus generation (for 1 to 3 months); and
III. Cultivating the callus(es) obtained from step II in a MS medium (Murashige and Skoog Basal Medium, purchased from Sigma company, product number: M5519) at 25° C. and 50~60% of humidity (for 1 to 1.5 months).

The *Mesembryanthemum crystallinum* L. plants (IP) of batch B and the *Mesembryanthemum crystallinum* L. calluses (IPC) obtained from *Mesembryanthemum crystallinum* L. plants of batch A were subject to the following operations to prepare a *Mesembryanthemum crystallinum* L. plant (IP) extract and a *Mesembryanthemum crystallinum* L. callus (IPC) extract, respectively:
(1) Freeze-drying the *Mesembryanthemum crystallinum* L. plants (or *Mesembryanthemum crystallinum* L. calluses) at −22° C. for 12 hours;
(2) Crushing the freeze-dried *Mesembryanthemum crystallinum* L. plants (or *Mesembryanthemum crystallinum* L. calluses) of step (1) to provide a *Mesembryanthemum crystallinum* L. plant powder (or a *Mesembryanthemum crystallinum* L. callus powder);
(3) Mixing the *Mesembryanthemum crystallinum* L. plant powder (or the *Mesembryanthemum crystallinum* L. callus powder) obtained from step (2) with 70% ethanol solution at a weight ratio of ethanol solution: powder=10:1;
(4) Ultrasonic agitating the mixture obtained from step (3) at 70° C. for 30 minutes;
(5) Filtrating the mixture obtained from step (4) with a filter membrane to provide a filtrate;
(6) Heating the filtrate obtained from step (5) to 95° C. and maintaining at 95° C. for 20 minutes to sterilize; and
(7) Cooling the filtrate of step (6), and then keeping it in cold storage for use in the following experiments.

Example 2: Effects of *Mesembryanthemum crystallinum* L. Callus (IPC) Extract on Anti-Oxidation Human skin fibroblasts (CCD-966SK, purchased from ATCC) were cultivated in a MEM medium (purchased form Gibco, product number: 61100-061) for 24 hours, and then were divided into four groups for the following treatments:
(1) Control group: cells were cultivated in a MEM medium for 2 hours (i.e., the cells were cultivated in a medium without IP extract and IPC extract).
(2) $H_2O_2$ group: cells were cultivated in a MEM medium (i.e., the cells were cultivated in a medium without IP extract and IPC extract) for 1 hour, and then $H_2O_2$ was added into the medium to provide a final concentration of 1 mM to treat the cells for 1 hour.
(3) $H_2O_2$+IP group: cells were cultivated in a MEM medium being externally added with the IP extract obtained from Example 1 (to a final concentration of 2 mg/ml) for 1 hour, and then $H_2O_2$ was added in to the medium to provide a final concentration of 1 mM to treat the cells for 1 hour.
(4) $H_2O_2$+IPC group: cells were cultivated in a MEM medium being externally added with the IPC extract obtained from Example 1 (to a final concentration of 2 mg/ml) for 1 hour, and then $H_2O_2$ was added in to the medium to provide a final concentration of 1 mM to treat the cells for 1 hour.

Thereafter, each of the above cell groups was treated with DCF-DA dye for 15 minutes, and then was detected by flow cytometry for the fluorescence intensity. Since ROS can covert DCF-DA (non-fluorescent) into DCF (fluorescent), the measured fluorescence intensity can represent the ROS content in cells and a higher fluorescence intensity represents a higher level of ROS in cells. The result of control group was served as a basis for calculating the relative fluorescence intensity of other groups. The results are shown in FIG. 1 (*represents $p<0.05$, showing that there is a significant difference as compared to $H_2O_2$ group; ** represents $p<0.01$, showing that there is a significant difference as compared to $H_2O_2$ group; # represents $p<0.05$, showing that there is a significant difference as compared to $H_2O_2$IP group).

As shown in FIG. 1, as compared to the control group, the fluorescence intensity of $H_2O_2$ group significantly increased. However, as compared to $H_2O_2$ group, the fluorescence intensities of $H_2O_2$+IP group and $H_2O_2$+IPC group all significantly decreased. In addition, as compared to $H_2O_2$+

IP group, the fluorescence intensity of $H_2O_2$+IPC is significantly lower. These results indicate that an IPC extract can effectively decrease the oxidation stress of $H_2O_2$ and decrease the ROS levels in cells, and thus, can be used for anti-oxidation. Furthermore, the effects of an IPC extract is significantly better than that of an IP extract.

Example 3: Effects of *Mesembryanthemum crystallinum* L. Callus Extract on Delaying Skin Cell Aging, Nursing Skin, and Repairing Skin (3-1) Treatment of Human Skin Fibroblasts Human skin fibroblasts (CCD-966SK; purchased from ATCC) were cultivated in a MEM medium for 24 hours, and then were divided into four groups for the following treatments:
(1) Control group: cells were cultivated in a MEM medium for 48 hours (i.e., the cells were cultivated in a medium without IPC extract).
(2) UVA+6 hr group, UVA+24 hr group, UVA+48 hr group: cells were cultivated in a MEM medium being externally added with the IPC extract obtained from Example 1 (to a final concentration of 2 mg/ml) for 6 hours, 24 hours and 48 hours, respectively.
Thereafter, each of the above cell groups were irradiated with UVA for 1 hour.

(3-2) Anti-Photoaging and Anti-Oxidation

To further ascertain the effects of *Mesembryanthemum crystallinum* L. callus extract provided in accordance with the present invention on anti-photoaging and anti-oxidation, qRT-PCR was conducted after completing Example 3-1 to detect the expression levels of antioxidant genes such as CAT-1 and SOD2-1 in the cells of each group. The results of control group were served as a basis for calculating the relative gene expression of other groups. The results are shown in FIG. 2.

Figure 2:
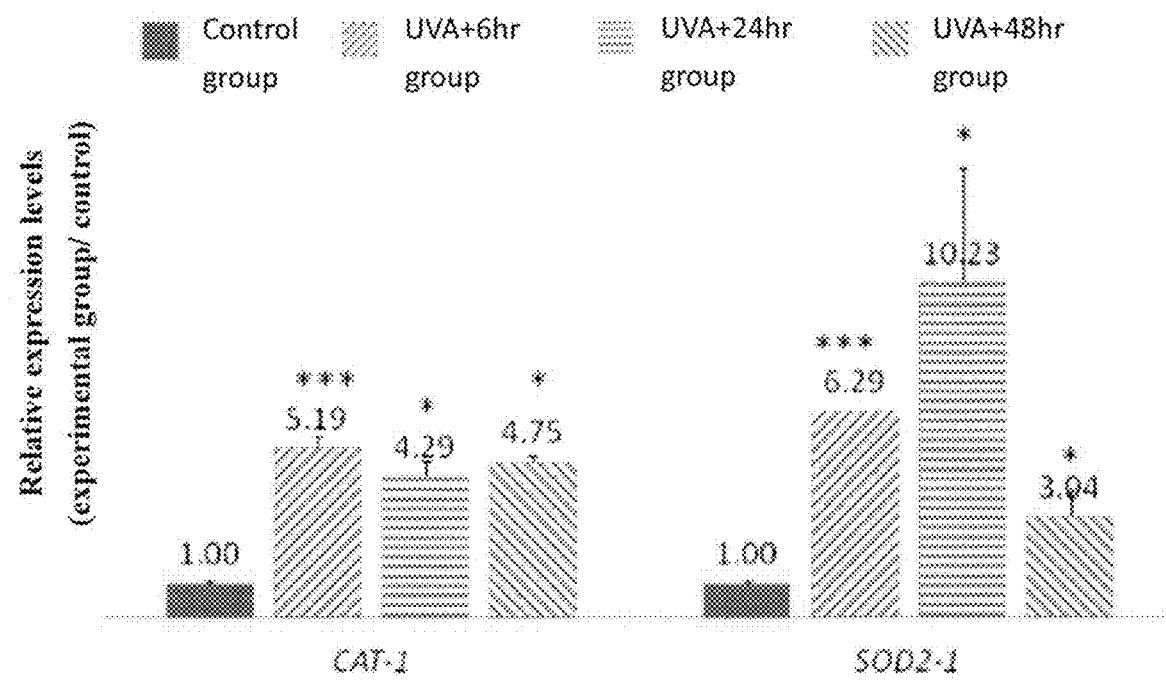
FIG. 2 illustrates the results of qRT-PCR (real-time quantitative polymerase chain reaction), showing the expression levels of CAT-1 and SOD2-1 genes of human skin fibroblasts.

As shown in FIG. 2, as compared to the control group (without *Mesembryanthemum crystallinum* L. callus extract treatment), the expression levels of antioxidant genes (i.e., CAT-1 and SOD2-1) of the groups treated with *Mesembryanthemum crystallinum* L. callus extract (including UVA+6 hr group, UVA+24 hr group, UVA+48 hr group) all significantly increased. This result indicates that *Mesembryanthemum crystallinum* L. callus extract has effects on anti-photoaging and anti-oxidation, and thus, can be used for delaying skin cell aging.

(3-3) Repairing DNA

The damage caused by DNA mutation or breakage can be avoided in an organism because there are DNA repair mechanisms such as base excision repair (BER), nucleotide excision repair (NER), and double-strand break end joint (DSB) in the organism.

To ascertain whether the *Mesembryanthemum crystallinum* L. callus extract provided in accordance with the present invention can repair DNA, in addition to the expression levels of antioxidant genes such as CAT-1 and SOD2-1, the expression levels of genes related to the mechanisms such as BER, NER and DSB in cells of each group were also detected in the qRT-PCR conducted after Example 3-1. The results are shown in FIGS. 3A to 3C ($*p<0.05$, $p<0.01$, $*P<0.001$).

Figure 3A:
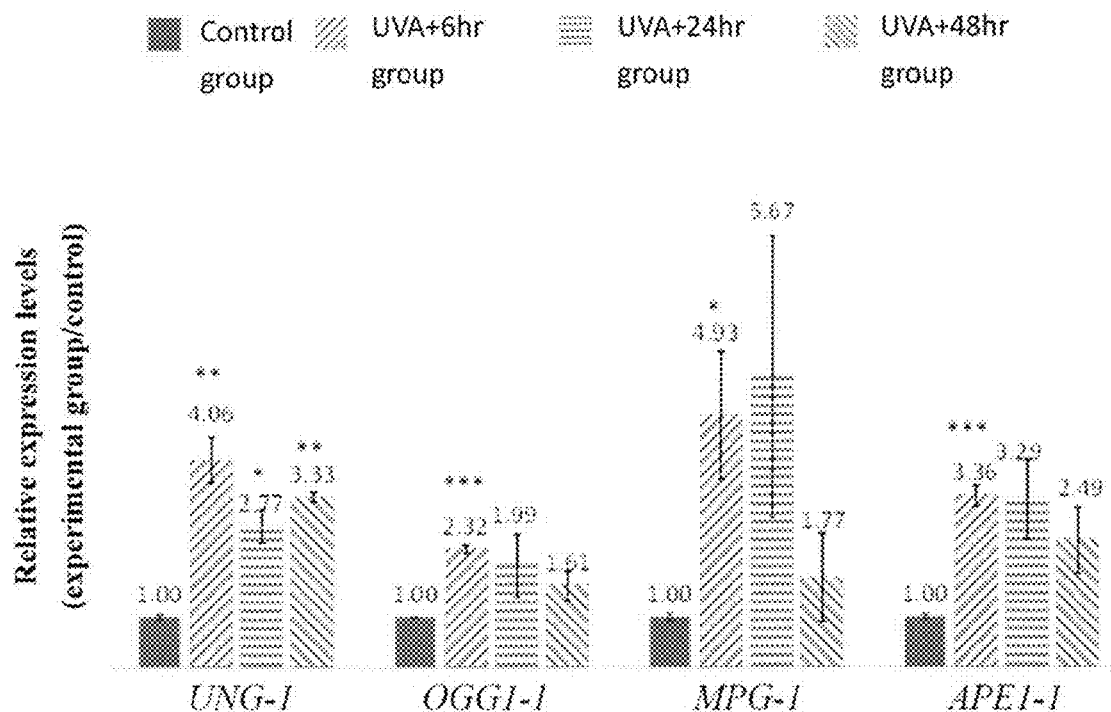
FIGS. 3A to 3C are the results of qRT-PCR, showing the expression levels of BER related genes (including UNG-1, OGG1-1, MPG-1 and APE1-1), NER related genes (including ERCC1-1, ERCC6-1 and XPA-1), and DSB related genes (including XRCC1-1 and XRCC5-1) of human skin fibroblasts.
Figure 3B:
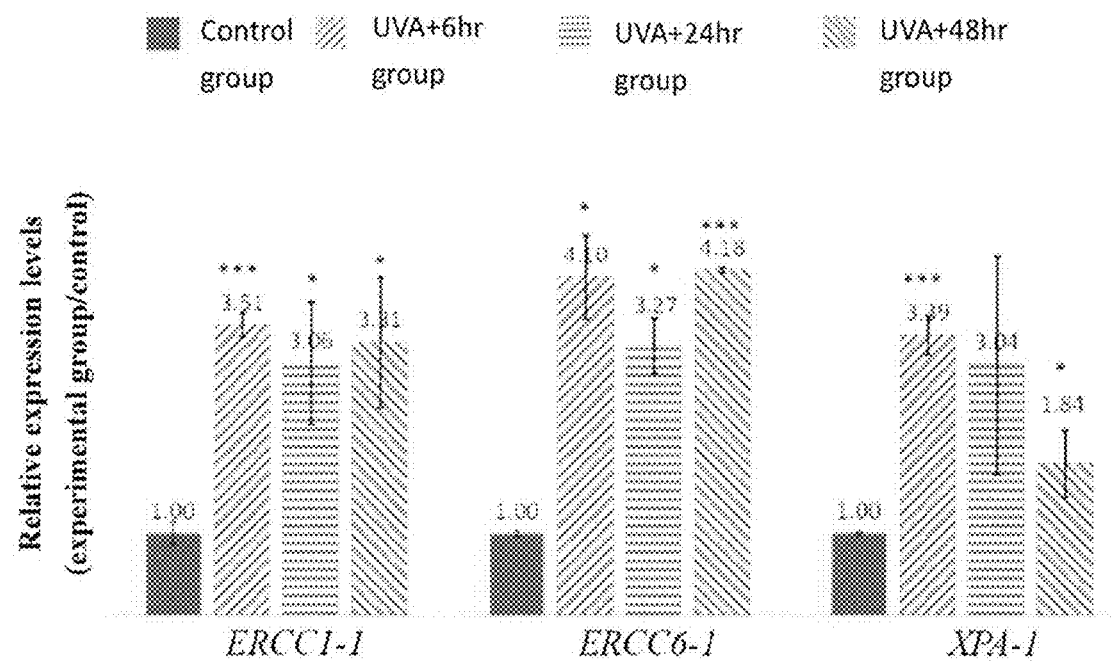
Figure 3C:
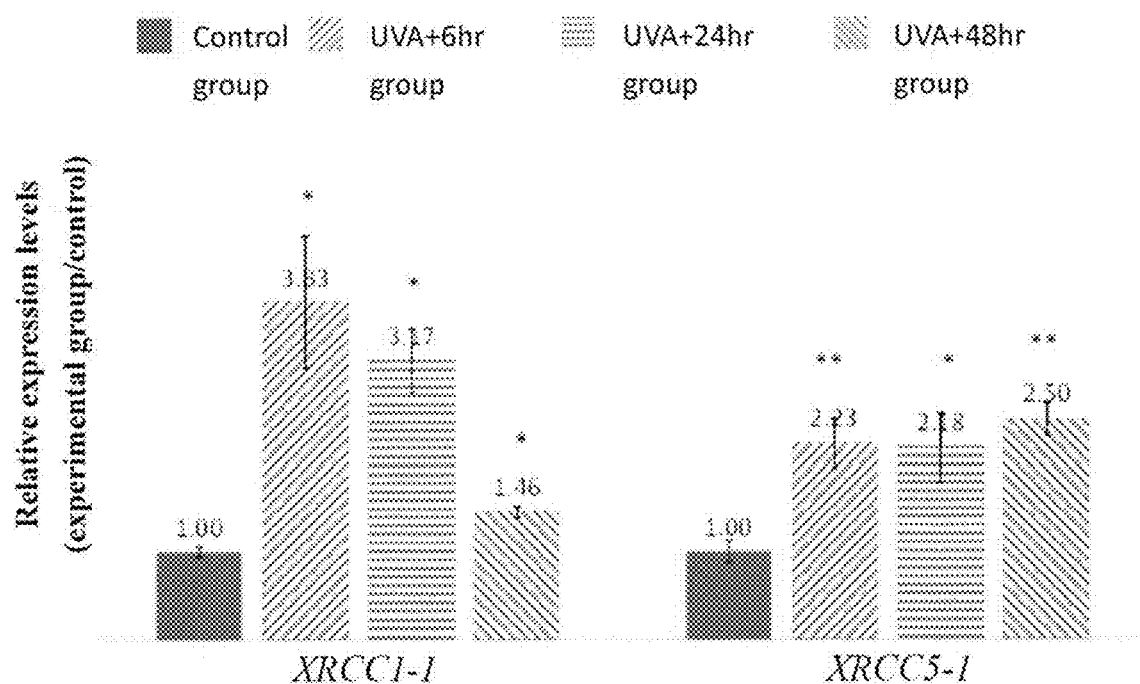

As shown in FIGS. 3A to 3C, as compared to the control group, the expression levels of BER related genes (including UNG-1, OGG1-1, MPG-1, and APE1-1), NER related genes (including ERCC1-1, ERCC6-1, and XPA-1), and DSB related genes (including XRCC1-1 and XRCC5-1) of the groups treated with *Mesembryanthemum crystallinum* L. callus extract all significantly increased. These results indicate that *Mesembryanthemum crystallinum* L. callus extract can effectively repair DNA, and thus, the effect of delaying skin cell aging can be achieved.

(3-4) Protecting DNA

It is known that when the DNA of the cells is damaged, a tailing phenomenon can be noted form the result of unicellular electrophoresis. The level of DNA damage can be assessed by calculating the proportion of cells with the tailing phenomenon.

To further ascertain whether the *Mesembryanthemum crystallinum* L. callus extract provided in accordance with the present invention can protect the DNA of cells, unicellular electrophoresis was conducted on cells of the control group, $H_2O_2$ group and $H_2O_2$+IPC group in Example 2. The results are shown in FIGS. 4A and 4B ($**p<0.01$).

Figure 4A:
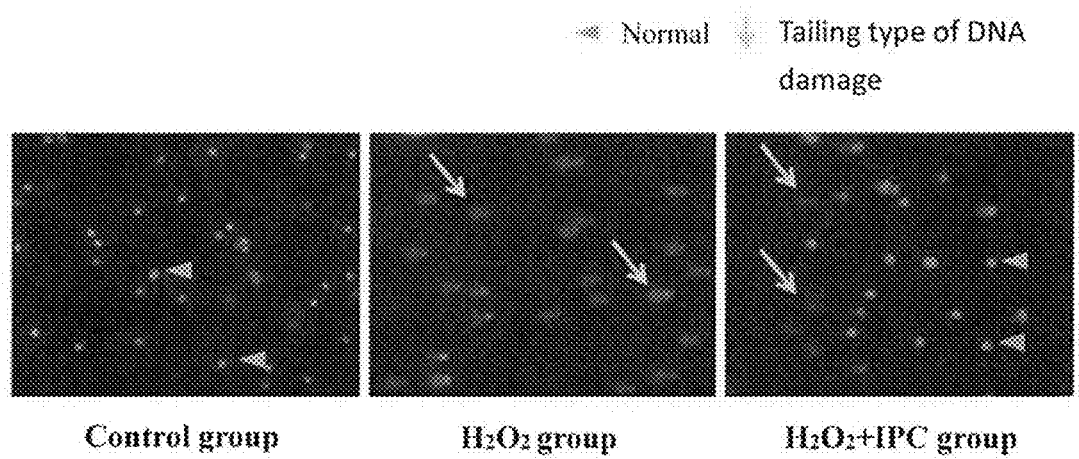
FIGS. 4A and 4B are the results of unicellular electrophoresis, showing the DNA damage of cells.
Figure 4B:
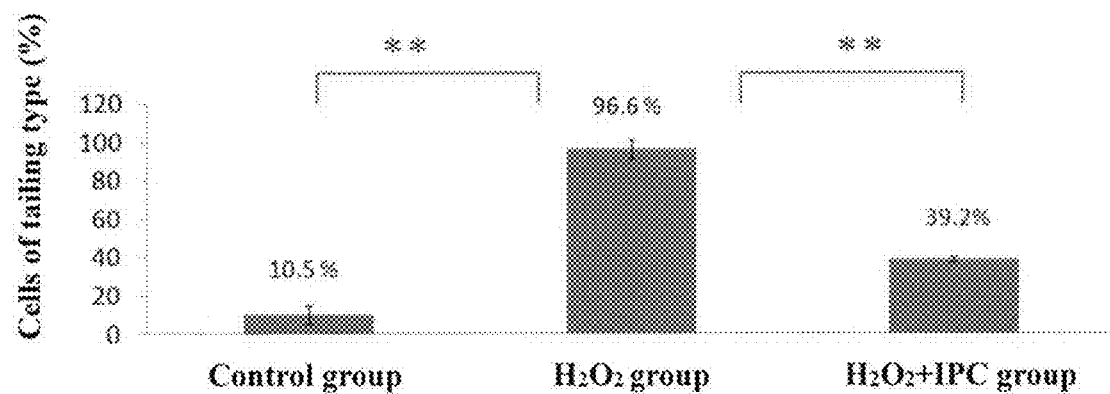

As shown in FIGS. 4A and 4B, as compared to the control group, the proportion of cells with tailing phenomenon (i.e., DNA damage) in the $H_2O_2$ group is significantly higher. However, as compared to the $H_2O_2$ group, the proportion of cells with tailing phenomenon in $H_2O_2$+IPC group is significantly lower. These results indicate that *Mesembryanthemum crystallinum* L. callus extract can effectively protect the DNA of cells, and thus, the effect of delaying skin cell aging can be achieved.

(3-5) Alleviating Degradation and Wasting of Collagen

Degradation and wasting of collagen will accelerate skin aging. It is known that an increment in expression level of TIMP1 gene represents an inhibition of collagen degradation, and an increment in expression level of COL1A represents an increment in the expression level of collagen. To further ascertain whether the *Mesembryanthemum crystallinum* L. callus extract provided in accordance with the present invention can alleviate the degradation and wasting of collagen in skin, the expression levels of TIMP1 and COL1A1 in cells of the control group and UVA+24 hr group were also detected in the qRT-PCR conducted after Example 3-1. The results of control group were served as a basis for calculating the relative gene expression levels of UVA+24 hr group. The results are shown in FIG. 5 ($*p<0.05$, $**p<0.01$).

Figure 5:
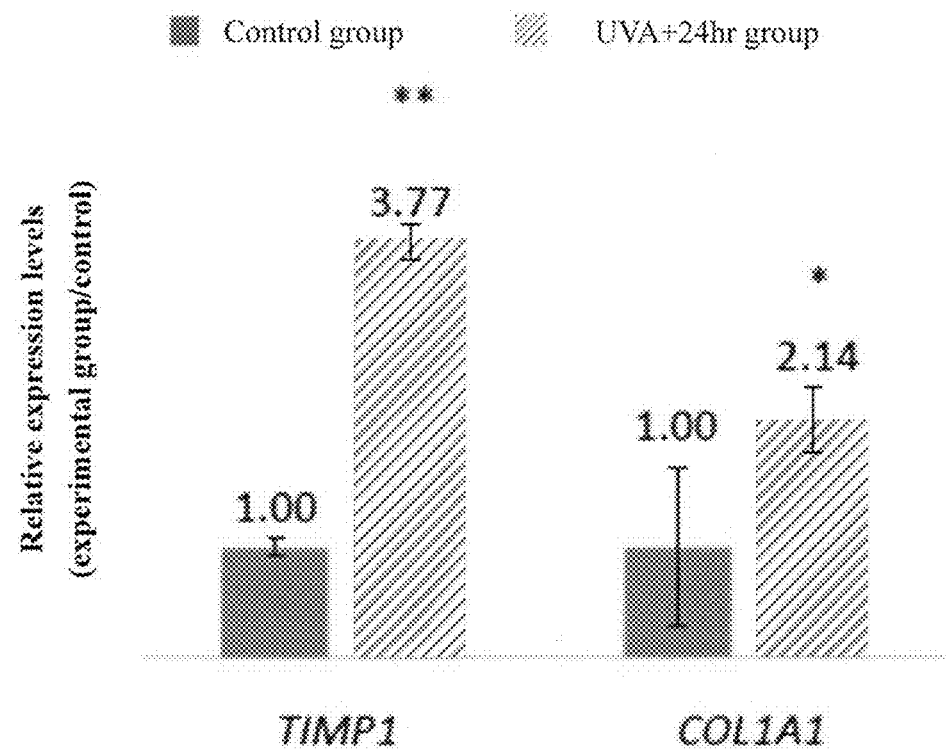
FIG. 5 illustrates the results of qRT-PCR, showing the expression levels of TIMP1 and COL1A1 genes of human skin fibroblasts.

As shown in FIG. 5, as compared to the control group, the expression levels of TIMP1 and COL1A1 of UVA+24 hr group significantly increased. This result indicates that *Mesembryanthemum crystallinum* L. callus extract can effectively decrease degradation of collagen and increase synthesis of collagen, and thus, can be used for alleviating degradation and/or wasting of collagen to achieve the effects of nursing and repairing skin.

(3-6) Increasing Survival Rate of Human Skin Fibroblasts

Human skin fibroblasts were cultivated in a MEM medium for 24 hours, and then divided into six groups for the following treatments:
(1) Control group: cells were cultivated in a MEM medium for 24 hours (i.e., the cells were cultivated in a medium without IPC extract).
(2) UVA group: cells were cultivated in a MEM medium for 24 hours (i.e., the cells were cultivated in a medium without IPC extract) and then irradiated with UVA for 1 hour.
(3) UVA+0.75 group, UVA+1 group, UVA+1.5 group and UVA+2 group: cells were cultivated in a MEM medium being externally added with the IPC extract obtained from Example 1 (to a final concentration of 0.75, 1, 1.5 and 2 mg/ml, respectively) for 24 hours, and then irradiated with UVA for 1 hour.

Figure 6A:
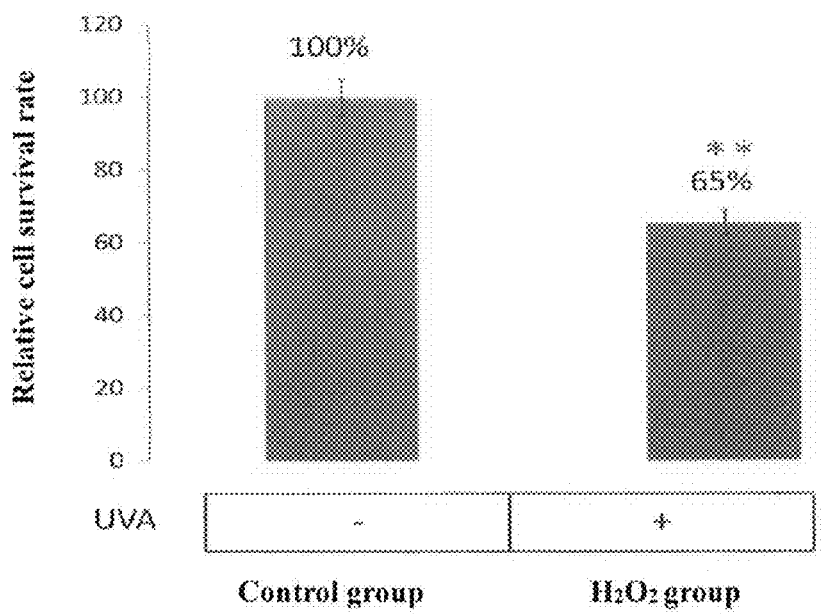
FIGS. 6A and 6B illustrate the results of the MTT assay, showing the survival rate of human skin fibroblasts.
Figure 6B:
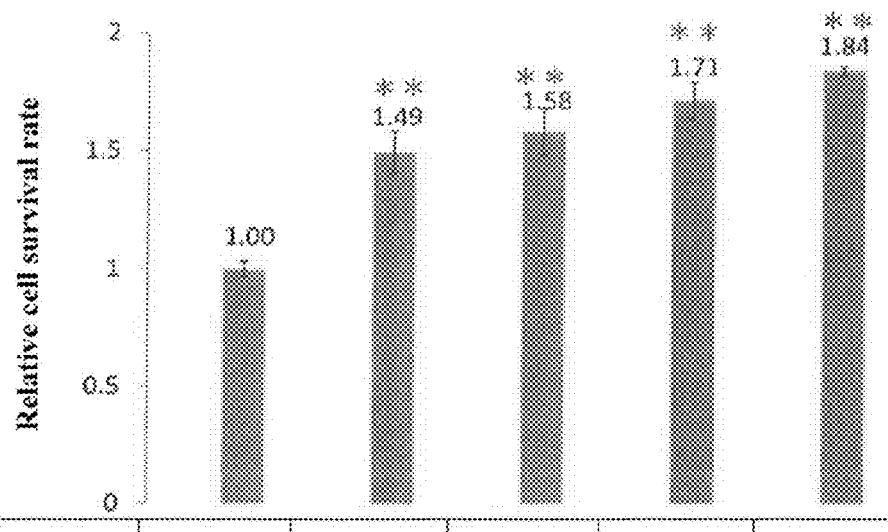

Thereafter, each of the above cell groups was determined by the MTT assay for the cell survival rate. The results are shown in FIGS. 6A and 6B (**p<0.01). As shown in FIG. 6A, as compared to the control group, the cell survival rate of the UVA group is significantly lower. However, as shown in FIG. 6B, as compared to the UVA group, the cell survival rate of the groups treated with *Mesembryanthemum crystallinum* L. callus extract (including UVA+0.75 group, UVA+1 group, UVA+1.5 group and UVA+2 group) all significantly recovered, and the concentration of *Mesembryanthemum crystallinum* L. callus extract was proportional to the cell survival rate. These results indicate that *Mesembryanthemum crystallinum* L. callus extract can effectively reduce the UVA-induced damage to the cells, and that the *Mesembryanthemum crystallinum* L. callus extract of an experimental concentration is not toxic to normal human skin fibroblasts.

(3-7) Reducing Skin Texture 10 volunteers were subjected to the analysis of Skin analyzer TD and DermaLab® Combo ultrasonic analyzer at Week 0 (i.e., prior to being applied with the essence) for their skin texture, skin pores, and transepidermal water loss. Thereafter, each volunteer applied the essence (containing 1 wt % of *Mesembryanthemum crystallinum* L. callus extract obtained from Example 1) over half of their faces and applied the placebo (does not contain the *Mesembryanthemum crystallinum* L. callus extract provided in accordance with the present invention, but contain the other components of the essence) to the other half of their faces each day and night for 6 weeks, and then tested their skin texture (i.e. fine lines), skin pores, and transepidermal water loss for comparing to those of Week 0. The results are shown in Table 1 and FIG. 7.

TABLE 1

| Test items | Results of applying essence for 6 weeks (as compared to those of Week 0) | Results of applying essence for 6 weeks (as compared to those of smearing placebo) |
| --- | --- | --- |
| Texture | Reducing 19.5% | Reducing 16.8% |
| Skin pores | Shrinking 19.7% | Shrinking 16.6% |
| Transepidermal Water loss | Decreasing 18.4% | Decreasing 9.9% |

Figure 7:
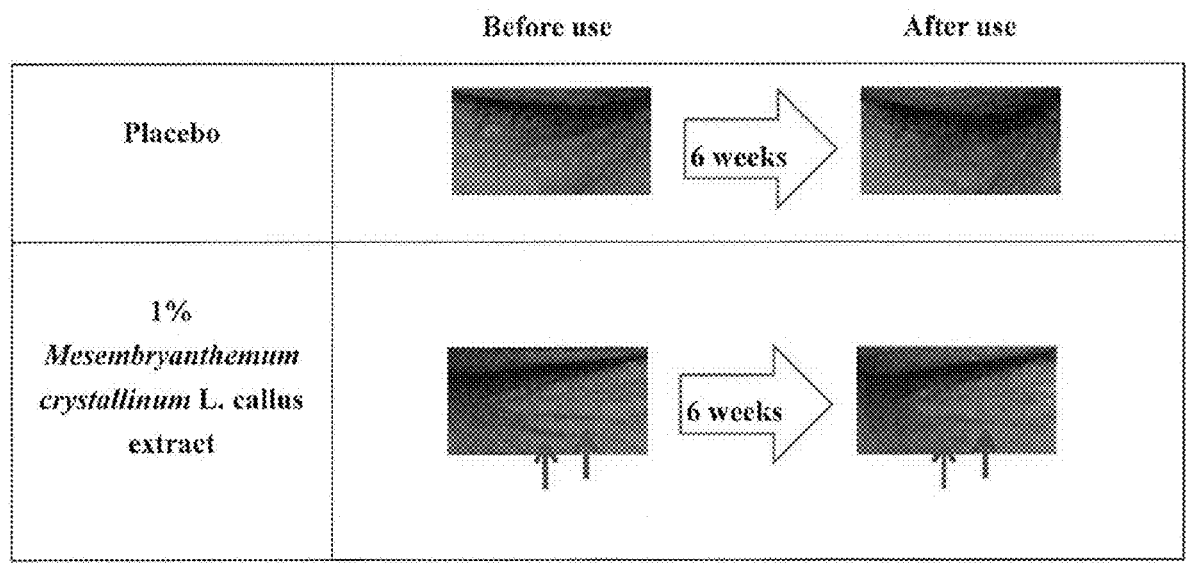
FIG. 7 shows the results of using Skin analyzer TD to detect the skin texture.

As shown in Table 1, 6 weeks after using the essence being externally added with the *Mesembryanthemum crystallinum* L. callus extract provided in accordance with the present invention, the skin texture significantly reduced, skin pores significantly shrunk, and transepidermal water loss significantly decreased. In addition, as shown in FIG. 7, as compared to applying the placebo, fine lines around the eyes significantly reduced after applying the essence (containing *Mesembryanthemum crystallinum* L. callus extract of the present invention) for 6 weeks. These results indicate that the *Mesembryanthemum crystallinum* L. callus extract provided in accordance with the present invention indeed has effects on nursing and repairing skin.

Example 4: Effect of *Mesembryanthemum crystallinum* L. Callus Extract on Treating and Preventing Melanoma Melanoma cells (purchased from ATCC, product number: CRL-6475) were cultivated for 24 hours, and then divided into six groups. One of the six groups was continuously cultivated in a DMEM medium (purchased from Gibco, product number: 12100-046) without *Mesembryanthemum crystallinum* L. callus extract for 48 hours (served as "control group"), and the other five groups were respectively cultivated in a DMEM medium being externally added with the *Mesembryanthemum crystallinum* L. callus extract obtained from Example 1 (the final concentration of *Mesembryanthemum crystallinum* L. callus extract in the medium were 0.25, 0.5, 1, 2 and 4 mg/ml, respectively) for 48 hours. Thereafter, each of the above cell groups was determined by the MTT assay for the cell survival rate. The result of the control group was served as a basis for calculating the relative survival rate of other groups. The results are shown in FIG. 8 (**p<0.01).

Figure 8:
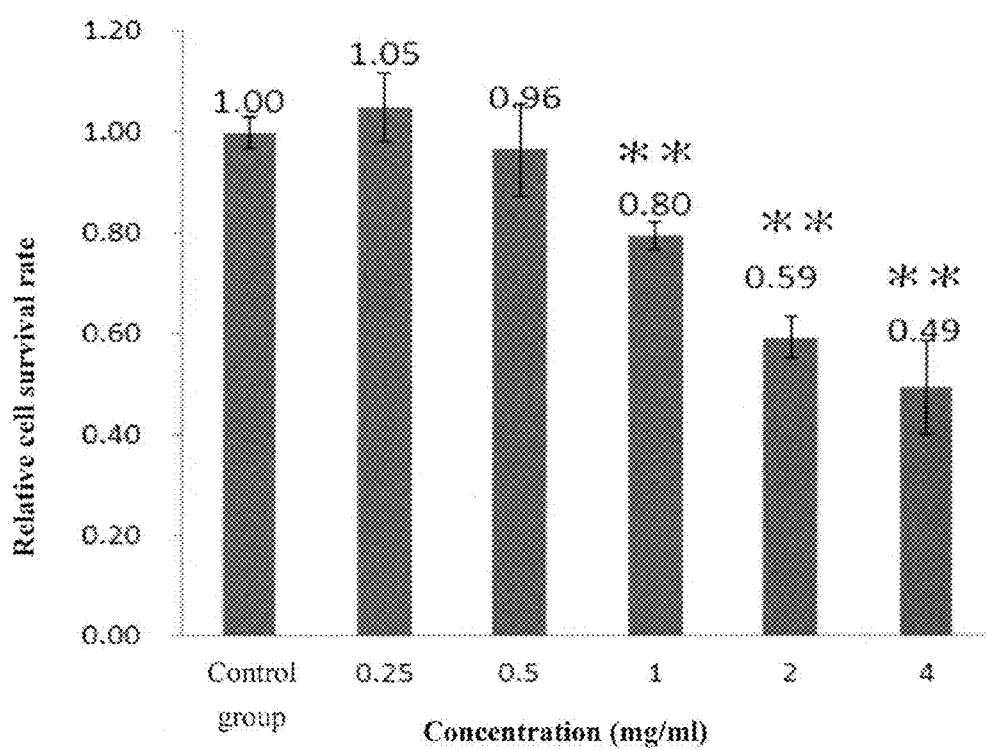
FIG. 8 illustrates the results of the MTT assay, showing the survival rate of melanoma cells.

As shown in FIG. 8, when the final concentration of *Mesembryanthemum crystallinum* L. callus extract in the medium was higher than 0.5 mg/ml, the survival rate of melanoma cells is inversely proportional to the concentration of *Mesembryanthemum crystallinum* L. callus extract. These results indicate that *Mesembryanthemum crystallinum* L. callus extract can effectively kill melanoma cells, and thus, can be used for treating and/or preventing skin cancer.

BRIEF DESCRIPTION OF REFERENCE NUMERALS

Not applicable.

DEPOSIT OF BIOLOGICAL MATERIAL

Not applicable.

SEQUENCE LISTING

Not applicable.

What is claimed is:

1. A method for delaying skin aging, improving skin, and/or repairing skin in a subject in need thereof, comprising administering to said subject in need thereof an effective amount of a *Mesembryanthemum crystallinum* L. callus extract, wherein the extract is a polar solvent extract of *Mesembryanthemum crystallinum* L. callus.

2. The method as claimed in claim 1, wherein the extract inhibits photoaging and oxidation, and repairs DNA.

3. The method as claimed in claim 1, wherein the extract decreases collagen degradation, decreases collagen wasting, and improves skin texture.

4. The method as claimed in claim 1, wherein the *Mesembryanthemum crystallinum* L. callus extract is administered as an essence or a beauty beverage.

5. The method as claimed in claim 4, wherein the concentration of the *Mesembryanthemum crystallinum* L. callus extract in the essence is from 0.1 to 10 wt %.

6. The method as claimed in claim 4, wherein the concentration of the *Mesembryanthemum crystallinum* L. callus extract in the beauty beverage is from 1 to 1000 ppm.

7. A method of treating skin cancer in a subject in need thereof, comprising administering to said subject an effective amount of a *Mesembryanthemum crystallinum* L. callus extract, wherein the extract is a polar extract of *Mesembryanthemum crystallinum* L. callus.

8. The method as claimed in claim 7, wherein the *Mesembryanthemum crystallinum* L. callus extract is transdermally or orally administered to the subject.

* * * * *